United States Patent [19]

Bierl

[11] Patent Number: 4,766,261

[45] Date of Patent: Aug. 23, 1988

[54] PURIFICATION OF FLUOROCARBONS

[75] Inventor: Thomas W. Bierl, Pittsburgh, Pa.

[73] Assignee: Adamantech, Inc., Linwood, Pa.

[21] Appl. No.: 805,596

[22] Filed: Dec. 10, 1985

Related U.S. Application Data

[63] Continuation of Ser. No. 650,679, Sep. 17, 1984, abandoned, which is a continuation-in-part of Ser. No. 547,314, Oct. 31, 1983, abandoned.

[51] Int. Cl.$^4$ .............................................. C07C 17/38
[52] U.S. Cl. .................................... 570/179; 570/177; 570/178; 570/180
[58] Field of Search ...................... 570/179, 180, 177

[56] References Cited

U.S. PATENT DOCUMENTS 3,391,201 7/1968 Jaeger .................................. 570/179
3,696,156 10/1972 Weeks .................................. 570/179

FOREIGN PATENT DOCUMENTS 13018 7/1966 Japan ................................... 570/262

OTHER PUBLICATIONS

Grafstein, Detection Estimation and Removal of Inpurities in Fluorocarbon Liquids, Analytical Chemistry, vol. 26, No. 3, Mar. 1954, pp. 523–525.

Primary Examiner—J. E. Evans
Attorney, Agent, or Firm—J. Edward Hess; Donald R. Johnson

[57] ABSTRACT

Fluorocarbons are purified and toxicity substantially reduced by contact with a substantially dry, strongly basic and strongly nucleophilic alkali or alkaline earth metal compound, and separating the decomposition products which form.

12 Claims, No Drawings

PURIFICATION OF FLUOROCARBONS

This application is a continuation of application Ser. No. 650,679 filed Sept. 17, 1984 and now abandoned which in turn is a continuation-in-part of application Ser. No. 547,314 filed Oct. 31, 1983 and now abandoned.

BACKGROUND OF THE INVENTION

This invention relates to the purification of fluorocarbon compounds to remove hydrogen-containing materials and/or to render the fluorocarbons less toxic to living organisms.

Biological applications of fluorocarbon compounds have expanded in recent years, therefore requiring careful attention to purification of the compounds to provide pharmaceutical grade material. Typical of such applications are the blood substitute and perfusion media uses of perfluorinated cyclic hydrocarbons described in U.S. Pat. Nos. 3,911,138—Clark and 4,105,798 —Moore and Clark. The latter patent describes the purification of a perfluoro polycyclic hydrocarbon mixture by refluxing with 10% aqueous potassium hydroxide (KOH). It is also known that fluorocarbons may be purified prior to biological evaluations by refluxing with 4N aqueous KOH for several hours to remove partially fluorinated, hydrogen-containing byproducts.

However, even with several treatments with fairly concentrated KOH solutions (about 30 wt.%), the known treatments have reduced the hydrogen content only about 30–50%, e.g., in one type of fluorocarbon from about 1000 ppm in the starting material to about 500–700 ppm in the product, and in another type from about 100 ppm in the starting material to about 50 ppm in the product. (In this specification, ppm of hydrogen means the weight of hydrogen atoms relative to the total weight of the fluorocarbon compounds determined by infrared spectroscopy.) Since it is now generally believed that for biological applications, especially for treatment of human medical conditions, the hydrogen content of the fluorocarbons should be less than about 25 ppm, preferably less than about 5 ppm, it is apparent that the conventional KOH purification procedure is inadequate, even though the conventional procedure, when measured by some toxicity test procedures, appears to substantially reduce or even eliminate toxicity in the purified product. The reason for this inadequacy is that substantial testing of perfluorocarbons in humans has not yet occurred. Therefore and also because toxicity is actually a function of both the nature of the species which contains hydrogen, as well as the hydrogen content, it is not known for sure what level of these hydrogen containing species can be regarded as non-toxic. Also, it is not known for sure whether hydrogen-containing species are toxic or, if not toxic, whether it reacts in the body to form something which is toxic. In view of the lack of knowledge about human toxicity, and the tremendous risks associated with erroneous judgments in respect thereof, the best solution is simply to remove as much of the hydrogen as possible and then evaluate the product on the basis of the amount of any residual hydrogen present and on toxicity tests of the product. In this regard the present process is much more effective in producing a less toxic product than the existing process.

"Purification" or similar term as used in this specification means elimination or substantial reduction of (1) acute toxicity as determined by in vitro tests such as the L-cell test or in vivo $LD_{50}$ test, and/or (2) hydrogen content.

In U.S. Pat. No. 3,696,156—Weeks, KOH or other base, deposited on an alumina carrier, is disclosed for treatment of lower molecular weight fluoroperhalocarbons, containing two to six carbon atoms. This patent discloses treating saturated fluoroperhalocarbons with an agent prepared by dissolving alkali metal hydroxide in just sufficient amount of water to wet the surface of alumina, driving off gross water by gentle heating and then heating from about 250° C. to about 400° C. in a stream of nitrogen. The purpose of the treatment is to remove toxic unsaturated impurities such as octafluorobutenes, so that the fluoroperhalocarbon product will be sufficiently non-toxic for use as an aerosol propellant. There is no disclosure that the treating agent would be effective to solve the toxicity problems connected with hydrogen-containing compounds contained as impurities in higher molecular weight fluorocarbons which are useful as blood substitutes.

SUMMARY OF THE INVENTION

It has now been found that perfluorocarbons can be purified to levels required for biological uses by reaction with a strongly basic and strongly nucleophilic compound wherein the compound contains no more than 30 wt. % water, as opposed to the 5–30 wt.% KOH solutions of prior art purification techniques for such perfluorocarbons. In the purification process the hydrogen-containing molecules and/or other impurities are reacted with the basic compound and the reaction products are separated from the perfluorocarbon molecules. "Perfluorocarbons", as the term is used herein, refers to fluorinated organic compounds containing no hydrogen in the molecule. "Fluorocarbons" on the other hand include, in addition to perfluorocarbons, fluorinated organic compounds containing hydrogen in the molecule. The expressions perfluoro and F are synonymous.

A major benefit of the purification technique of the invention is the ability to achieve a higher purity with essentially a single reaction with the base (in the case of fluorocarbons containing about 100–200 ppm hydrogen) than can be obtained with the multiple reactions and extractions employed in prior processes. Fewer reactions also has the concomitant advantages of less opportunity for loss of desired product and lower production cost. The novel reaction will also facilitate obtaining even higher levels of purity than in prior purification processes, by adjustment of treatment conditions, such as temperature, work-up procedures, and in the case of fluorocarbons containing higher amounts of hydrogen, e.g., over 200 ppm, one or more repetitions of the reaction. These and other aspects will be detailed in the description which follows.

DETAILED DESCRIPTION

In accordance with the invention, perfluorocarbons are purified by contact with a strongly basic alkali metal and/or alkaline earth metal compound (groups I and II respectively or The Periodic Table). Suitable bases are those which have logarithmic basicity constants (pKb) of at least 12, preferably 13 to 14. It is believed that the bases have strong nucleophilic activity, sufficient for successful attack on the hydrogen containing molecule as described below. Compounds of lithium, sodium, potassium, magnesium, calcium, barium and strontium are preferred. Suitable compounds include hydroxides, oxides (both inorganic and organic metal oxides), as well as other compounds having adequate basicity.

Representative metal hydroxides are sodium hydroxide, potassium hydroxide, lithium hydroxide, magnesium hydroxide, calcium hydroxide, strontium hydroxide and barium hydroxide. Potassium hydroxide is particularly preferred. The organic metal oxides may be represented by the formula $M(OR)_x$ where M is the metal, R is alkyl or aryl (including aralkyl and alkaryl), and x is the valence of the metal M (1 or 2). The organic metal oxides can contain from 1 to about 20 carbon atoms in each R group, preferably 4–10. The higher the number of carbon atoms the easier the subsequent extraction of reaction residues becomes, as is shown hereinafter. The R groups independently may be straight or branched chain, alicyclic or aromatic, including combinations of aliphatic, alicyclic and aromatic groups, and may carry substituents containing hetero atoms (such as halogen) provided such substituents do not detract from the essential properties of the compounds in the present invention. Typical R groups are $C_1$-$C_8$ alkyl such as methyl, ethyl and propyl; cycloalkyl such as cyclohexyl and cycloheptyl; and aryl groups such as phenyl, naphthyl, benzyl and phenethyl, and groups of the foregoing types substituted with halogen, such as fluoro, chloro and bromo, or nitro. A variety of metal aryloxides and alkoxides are known which are useful in the process. Some of these are described and listed in the technical literature, such as Kirk-Othmer, Encyclopedia of Chemical Technology, Second Edition (1963), 1, 839, and include the methoxides, ethoxides and phenoxides of lithium, sodium, potassium and magnesium.

The strongly basic compounds employed according to the invention may contain water, in amount not exceeding about 30 wt. %. In the case of metal hydroxides, the amount may be such as to manifest a slightly tacky or pasty condition, but not a syrupy or other liquid state. In the case of the metal oxides, the amount of water is generally less than the amount, e.g. about 5 wt. %, which will substantially hydrolyze the oxide. The compound may be used in pellet form, but other forms are useful such as powders or flakes. The compound may also be used by dispersing or dissolving the same in a non-aqueous solvent (such as an alcohol, ether or ketone) to improve contact between the fluorocarbon and base phases of the reaction mixture provided, of course, that the solvent does not substantially diminish the strongly basic and strongly nucleophilic character of the base, e.g., by complex formation or other interaction between solvent, base and/or fluorocarbon.

In connection with the strong basicity and nucleophilicity of the bases, it is believed that the excellent purification achieved by the process of the invention is probably obtained by the following stepwise mechanism, although the invention is not to be limited by any theory. In the first step the fluorocarbon is attacked by the base which has the ability to remove even the most strongly bonded hydrogen atoms in a molecule which is otherwise highly fluorinated. The removal of the hydrogen results in a negatively charged fluorinated ion which is unstable. Consequently, it undergoes a molecular rearrangement with the resultant elimination of a fluoride ion and the stabilization of the molecule as a perfluoro-olefin. In the second step, the hydroxyl or alkoxide ion of the base, acting as a strong nucleophile, attacks the olefin at the double bond, adding to the molecule of hydroxyl or other functional group and again changing the molecule into an unstable negative ion which rearranges to form another olefin. In the special case where the attacking base is a metal hydroxide and the hydroxyl functional group is on a carbon which also has fluorine bonded to it, hydrogen fluoride is most probably eliminated forming a ketone. In Step 3 the olefin formed in Step 2 is again attacked by hydroxyl ion and the process continues as described above until the fluorine is nearly completely stripped from the carbon skeleton. The resulting species is highly oxygenated, resulting in its being partitioned into the water phase and out of the fluorocarbon phase in the subsequent extraction step, leaving behind the purified fluorocarbon.

Compounds which are not as strongly basic as those of the invention and not used in a substantially dry state are not capable of reacting with all of the different possible hydrogen positions in the molecule. If the hydrogen is not removed, the chain reaction is not initiated and the purification is not achieved. Moreover, if the anion of the metal hydroxide or organic metal oxide is not a strong nucleophile, it will not propagate the chief reaction by attacking the olefin formed during the first rearrangement. Without this nucleophilic addition to the double bond, the perfluoro olefin is not removable from the remaining saturated perfluorocarbon. It is this addition of the hydroxyl, alkoxide or aryloxide ion of the strong base which allows the final reaction products to be selectively extracted by either water or organic solvent.

The fluorocarbon feed material to the process of the invention is reaction product from the fluorination of carbon compounds, normally hydrocarbons, which product contains perfluorinated molecules not subject to attack by strongly basic and strongly nucleophilic compounds and some other fluorinated molecules or other substances which contain hydrogen and are therefore subject to such attack. They are impure perfluorocarbons, but are sometimes referred to as perfluorocarbons even though the latter description is not strictly accurate if there is any hydrogen present. The carbon compounds are aliphatic (cyclic or acyclic) hydrocarbons and/or hetero atom containing aliphatic carbon compounds, which, except for the residual hydrogen and/or toxic components, have been fully fluorinated. The compounds or mixtures may be in the vapor or liquid state at ambient temperatures and pressures. Solid compounds are purifiable in accordance with the invention by dispersion or dissolution in a liquid medium, by melting or by vaporization.

The invention has special significance for the purification of the blood substitute perfluorinated cyclic hydrocarbons described in U.S. Pat. Nos. 3,911,138 and 4,105,798, (both incorporated herein by reference) but the technique is also applicable to other fluorinated compounds such as are described in U.S. Pat. Nos. 3,823,091, 3,962,439 and 4,325,972.

Preferred perfluorocarbons for treatment according to the invention, are those which contain 7 to 18 carbon atoms in the molecule, and more preferably those which contain 9 to 18 carbon atoms, because such perfluorocarbons are suitable for use in biological applications. Representative compounds are the perfluorinated derivatives of chemically inert monocyclic compounds such as isopropylcyclopentane or isopropylcyclohexane, and $C_9$-$C_{18}$ polycyclic compounds such as bicyclononanes (e.g., bicyclo [3.3.1] nonane, 2,6-dimethylbicyclo [3.3.1] nonane, 3-methylbicyclo [3.3.1] nonane and trimethylbicyclo [3.3.1] nonane); adamantane and alkyl ($C_1$-$C_6$) adamantanes such as methyl and dimethyladamantane, ethyl and diethyladamantane, trimethyladamantane, ethylmethyladamantane, ethyldimethyladamantane and triethyladamantane; methyldiadamantane and trimethyldiadamantane; methyl and dimethylbicyclooctanes; tetrahydrobinor-S, pinane, camphane, decalin and alkyl decalins such as 1-methyldecaline; and 1,4,6,9-dimethanodecalin; bicyclo [4.3.2] undecane, bicyclo [5.3.0] decane, bicyclo [2.2.1] octane, tricyclo [5.2.1.0$^{2,6}$] decane, methyltricyclo [5.2.1.0$^{2,6}$] decane, and the like; or any mixtures thereof. Hetero atom perfluoro compounds include perfluoro ethers such as F-2-butyltetrahydrofuran, F-2-butylfuran, F-hydrofuran, the 1,2,2,2-tetrafluoromethyl ether of F-(2,5,8-trimethyl-3,6,9-trioxa-1-dodecanol) and F-n-methyl-morpholine. Acyclic aliphatic compounds include F-n-heptane and homologs.

Certain of the fluorine atoms of the foregoing materials may be substituted by other halogen atoms such as bromine as in perfluorobromo compounds. Included examples of these compounds are monobrominated compounds such as 1-bromo-pentadecafluoro-4-isopropylcyclohexane, 1-bromotridecafluoro-hexane, 1-bromo-pentadecafluorooctane and 1-bromo-pentadecafluoro-3-isopropylcyclopentane and perfluoro-1-bromobutylisopropyl ether; or polybrominated derivatives thereof.

As indicated above, the invention is applicable to fluorocarbons in the liquid or vapor state. However, solid compounds are treatable in accordance with the invention by dissolving in a suitable solvent or by melting or vaporization. Typical of such solid compounds are perfluoroadamantane and perfluorodimethyladamantane with relatively low levels of hydrogen contamination. These compounds may be dissolved in liquid perfluorocarbons (or other solvent), the purification of which may also be desired, and the resulting solution then treated. Suitable liquid fluorocarbons useful as solvents at F-decalin, F-tricyclo [5.2.1.0$^{2,6}$] decane, F-menthane, F-1-methyldecaline and F-alkyladamantanes, including any mixtures thereof.

In the process of the invention, mixtures comprising perfluorocarbons and other fluorocarbons containing hydrogen in the molecule are treated with a base of an alkali or alkaline earth metal. The base contains not more than about 30 wt. % of water, and reacts with such other compounds to convert the latter to reaction products which are separated from unreacted perfluorocarbons. The toxicity and/or the amount of compounds containing hydrogen is reduced.

The method of the invention is conveniently practiced by adding the base to the fluorocarbon to be purified in a reaction vessel (preferably glass or glass-lined) equipped with an agitator, and heating the mixture with agitation to an elevated temperature sufficient to react the base with components of the fluorocarbon mixture. Preferably, the temperature is in the range from about 165° C. to about 250° C. At temperatures at or above 250° C., some decomposition of the perfluorocarbons may take place, particularly with metal reactors, so such temperatures are not preferred. The reaction is maintained at the selected temperature for several minutes to several hours, e.g., about 1-5 hours. A typical temperature is about 170°-180° C. and a typical reaction time at this temperature is about 1-2 hours. However, both temperature and reaction time will depend on the specific fluorocarbon and the strong base. Since fluorocarbons for use in intravenous applications have relatively low vapor pressures and high boiling points, reflux temperature is often sufficient. Lower boiling fluorocarbons can be equivalently purified by heating the reaction mixture under pressure. Pressure reactors may also be useful if treatment of a fluorocarbon in the vapor state is desired, or pressure can be used to permit higher reaction temperature by elevating the boiling points of the liquids.

The foregoing reaction conditions are effective for a strong base such as KOH containing about 15 wt. % water and a reaction mixture containing about 15-25 wt. % of such base, based on fluorocarbons containing about 95 ppm or less of hydrogen. A higher concentration of a base such as KOH may be used for purification of such fluorocarbons, but no appreciable advantage is obtained. As indicated, the reaction conditions will, of course, be modified to fit other fluorocarbons, bases containing other amounts of water or other solvent, and other proportions of reactants. The skilled practitioner can make such modifications without undue effort. Generally, if the fluorocarbon to be purified has a higher proportion of hydrogen-containing material, more vigorous reaction conditions, and/or higher proportions of base to fluorocarbon will be used or the reaction may be repeated. Elevated temperatures normally are required to obtain a desirable rate and degree of reaction.

During the reaction the purification can be followed by separating treated PFC from the reaction mixture in the manner described below, and then testing the PFC for color with diethylamine (DEA) or for hydrogen or olefin by infrared. Perfluorocarbons are colorless in the presence of DEA but are dark yellow, brown or black if hydrogen is present.

At the end of the reaction the mixture is cooled and water is added to dissolve any unreacted base, metal fluoride, and the highly oxygenated carbonaceous residue normally formed during the reaction. The addition of water causes the reaction mixture to form a top aqueous phase containing reaction products such as metal fluoride and degradation products, and a bottom fluorocarbon phase containing the substantially purified fluorocarbon. The phases may be separated by any suitable liquid/liquid separation method such as decanting or the use of separatory funnels.

For medical applications a further final purification of the fluorocarbon may still be desirable for removal of trace amounts of reaction products. Such traces sometimes impart a haze to the product but may in any event be detected by analysis as noted above.

In the case of treatment with the organic metal oxides these traces of reaction product can be extracted by washing the fluorocarbon with a solvent such as a lower alkanol, ether or ketone after which any trace of solvent is washed out with water. This extraction with solvent is more effective when each R group of the organic metal oxide used contained from about 4 to 10 or more carbon atoms and this is one reason that such a range was described earlier as preferred.

A typical additional purification procedure, when KOH or other inorganic oxide was used is to react the residual impurities in the fluorocarbon with an organic carbonyl compound such as a ketone (e.g., acetone), organic acid (e.g., a $C_1$-$C_{10}$ monocarboxylic acid such as acetic acid) or an ester of such an acid and a $C_1$-$C_8$ alkanol such as methanol, ethanol or the like. From the resulting two-phase system the PFC phase is separated from the organic phase and is then washed with a water miscible $C_1-C_8$ alkanol (e.g., methanol, ethanol) acidified with an organic acid such as those described above. An acid/alkanol ratio of about 1:9 by weight is suitable but other ratios can also be used, e.g., about 1:50 to 1:1. A final wash with water is used to remove the traces of acid and alkanol remaining in the purified fluorocarbon.

The material resulting from the final purifications as described above will, if the starting PFC material contained not over about 200 ppm hydrogen, contain less than about 25 ppm hydrogen by infrared, usually less than 5, and will be essentially nontoxic as determined by in vitro toxicity tests (such as the L-cell test described below) and/or conventional intravenous $LD_{50}$ testing in mice.

The following examples are intended as further illustration of the invention without limiting the scope thereof, except as set forth in the appended claims.

EXAMPLE 1

Part A 4000 units by weight of a reaction mixture containing primarily perfluoro dimethyladamantane (F-DMA) and perfluoro trimethylbicyclononane (F-TMBCN), obtained by two pass, direct fluorination of DMA over cobalt trifluoride, and containing 95 ppm hydrogen is placed in a 5 liter, glass reaction flask equipped with a stirrer and a condenser vented to the atmosphere. The F-TMBCN was obtained as a result of ring-opening reactions occuring during the fluorination. 1000 units of 85% KOH (15% w/w $H_2O$) in pellet form are then added to the flask and stirring is commenced. Heat is applied to raise the temperature of the reaction mixture to reflux. The process takes about one hour to reach a final temperature of 170°–175° C. During this heating stage, the contents of the flask change in appearance: the pellets break up as the reaction progresses and the color of the slurry changes from clear with white solids, to amber, and then dark brown or black. Some water may also form as droplets in the condenser. After reflux is reached, the mixture is held at these conditions for about two hours, at which time the heat is shut off and the mixture is cooled to approximately 90° C. 2000 units of water are then slowly added to the flask, and the temperature of the mixture rises. The temperature rise is due to heat of dilution of the unreacted KOH. After the water addition is complete, the mixture is agitated to fully dissolve the solids which have become encrusted on the walls of the reaction vessel. Separation of the water phase, containing substantially all of the reaction products, from the fluorocarbon (PFC) phase is accomplished in a five liter separatory funnel. The two phases separate in about one hour. The fluorocarbon is then drained from the bottom of the separatory funnel and upon infrared analysis is found to contain less than 5 ppm hydrogen (limits of detection with the IR equipment used).

In an L-cell assay using Stock Littlefield strain L mouse fibroblasts as described by R. P. Geyer in his report for June 21, 1976 to June 20, 1978 under U.S. National Institutes of Health Contract No. N01-HB-6-2926, pages IV-1 to IV-6, the fluorocarbon product exhibits 6.7% inhibition of cell growth (ICG) as compared to the medium control (0% ICG). Medium control or assay control is medium plus cells dosed with additional medium equal in amount to the fluorocarbon in the test medium. Inhibition of cell growth theoretically ranges from 0 (no inhibition) to 100% (total kill) but 6.7% would generally be considered unsatisfactory in products intended for humans.

Part B

The fluorocarbon recovered in Part A above still has a slightly hazy appearance due to the presence of trace amounts of reaction product. Although the haze can be eliminated by conventional paper filtration, contact with the paper increases the toxicity (to 32.6% ICG) in the L-cell assay referred to in Part A above. Instead, the reaction product causing the haze is removed by treating the fluorocarbon phase in the following manner: 950 units of acetone is shaken in a separatory funnel for 5 minutes with the approximately 3800 units of product recovered from Part A. The fluorocarbon that is separated from the acetone has lost its hazy appearance, and any residual acetone is subsequently removed by washing with 950 units of a solution of acetic acid in methanol (1:9 by weight). Finally the trace level of methanol remaining is removed by treatment with 950 units of water. Both of these latter treatments are done in a manner similar to the acetone treatment described above. The final fluorocarbon product is free from haze and is found by infrared analysis to contain less than 5 ppm by weight hydrogen (limits of detection).

EXAMPLE 2

In this Example the fluorocarbon material was obtained similarly to the material in Example 1, except that in Example 2, the fluorination product was distilled to obtain a heart cut mixture richer in F-DMA, the weight ratio being about 3.5 F-DMA to 1 F-TMBCN. In addition the cytotoxicity test is the L-cell suspension culture assay, Protocol 745, of Hazelton Laboratories America, Inc., Vienna, Va. as described below. In this test procedure the assay control is cell culture and medium without fluorocarbon, the negative control is a fluorocarbon material purified as described in Example 1, Parts A and B, and having a low cytotoxicity as established by this assay, and the positive control is an untreated sample of fluorocarbon having known high toxicity.

L-Cell Test Procedure

The cell line is L-929, clone of strain L (CCL-1), the species of origin being the mouse, $C_3H/An$ (fibroblast). The cells are derived from the parenteral strain L established by W. R. Earle (J. National Cancer Institute 4:165, 1943). The source is American Type Culture Collection, ATCC L-929. The cells are maintained as frozen stocks in liquid nitrogen. Working stocks are maintained in suspension in modified Waymouth MB 752/1 Medium Complete (Waymouth MB 752/1 supplemented with 10% Bovine Serum, 1% Glutamine, 0.5% Gentamicin, 0.1% Pluronics, 0.03% Methylcellulose and 0.05% Darvan) at 37° C. in an atmosphere of 5% $CO_2$ and air, and passaged once a week. A test compound is tested neat at one dosage level, and both positive and negative controls are also tested along with an assay control (cell culture and medium, no fluorocarbon). Test compound and control materials are tested in quadruplicate.

For dosing, 50 ml. conical tubes are inoculated with test and control materials. Approximately $1-1.2 \times 10^5$ cells/ml in modified Waymouth's medium are added in 15 ml quantities to each conical tube and gently mixed. The caps are securely tightened and the tubes placed in a roller drum to permit complete rotation of the tube. The tubes are rotated at 37° C. for three days.

After three days incubation, aliquots of the cell cultures are diluted and stained with trypan blue. Using a hemacytometer, the cells are counted under a microscope to determine quantity and viability. Scoring is by averaging cell counts from each set of four replicates. From these results, the cell multiplication factor is determined. Inhibition of cell growth of the test compound as compared to the assay control cells is calculated. Percent inhibition of cell growth (% ICG) within five percentage units of the negative control values indicates lack of toxicity as compared to the negative control.

Percent inhibition of cell growth (ICG) is calculated as:

$$\% \ ICG = 100 - \% \ Growth$$

where $$\% \ Growth = \frac{Mean \ Cell \ Count \ of \ Treated \ Sample}{Mean \ Cell \ Count \ of \ Assay \ Control} \times 100$$

Similarly to Example 1, the fluorocarbon test material, after treatment in Part A, is contacted with paper, resulting in 51% ICG. The product is then treated as in Part B, resulting in −8% ICG (an actual increase in cell growth). Apparently, either the paper was contaminated with toxic material which then transferred to the sample, or the cellulose of the paper reacted in some manner to introduce toxicity into the Part A product. However, the Part B treatment removed the toxic components. The foregoing and other results are set forth in Table I below from which it can be seen that the test material showed essentially the same lack of cytotoxicity as the negative and assay controls (no significance is attached to negative ICGs).

TABLE I

| Sample | Dose per 15 ml of Media | ICG % |
|---|---|---|
| Assay Control | 1.5 ml | 0 |
| Negative Control | 1.5 ml | −5 |
| Positive Control | 0.75 ml | 100 |
| Test Material | 1.5 ml | −8 |

Assay Control: Cell culture and medium without fluorocarbon.
Negative Control: Cell culture and medium with fluorocarbon previously purified as in Example 1, Parts A and B.
Positive Control: Cell culture and medium with untreated sample of fluorocarbon.
Test Material: Cell culture and medium with fluorocarbon purified as in Example 2, Parts A and B.

EXAMPLE 3

A fluorocarbon material (PFC) purified as in Example 1, Parts A and B, and then emulsified is differentially tested for acute toxicity in mice (LD$_{50}$, Bioassay Systems Corp., Boston, Mass. with the results set forth in Table II. The fluorocarbon material was obtained similarly to the material in Example 2. It will be noted from the test results from Compositions C and D that the purified perfluorocarbon contributed no toxicity.

TABLE II

| | Aqueous[1] Composition (% w/v) | | LD$_{50}$(ml/kg)[2] |
|---|---|---|---|
| (A) | NaCl | 0.9 | ≧229 |
| (B) | NaCl | 0.9 | |
| | Glycerol | 1.0 | 138–229 |
| (C) | NaCl | 0.9 | |
| | Glycerol | 1.0 | |
| | Pluronic F-68 surfactant[3] | 3.5 | 118.4 |
| (D) | NaCl | 0.9 | |
| | Glycerol | 1.0 | |
| | Pluronic F-68 surfactant | 3.5 | |
| | PFC | 20.0 | 118.4 |

[1] Sterile water
[2] 95% confidence level, as practiced by Bioassay Systems Corp., Boston Massachusetts
[3] Polyoxyethylene - polyoxypropylene copolymer, molecular weight about 8200.

EXAMPLE 4

Comparative

A mixture of F-trimethylbicyclononane and F-dimethyladamantane, obtained as in Example 1 except using one-pass instead of two-pass fluorination, and therefore containing relatively high residual hydrogen (over 100 ppm), is treated ten times with 26.7% (w/w) KOH in water 105°–108° C., and is then extracted ten times at room temperature with 5% KOH solution. This is a prior art procedure. Table III below gives the L-cell toxicity results (Hazelton procedure as in Example 2) wherein the negative, positive and assay controls are the same as before (Table I). It will be seen that even multiple treatments with the 26.7% KOH, as representative of prior purification techniques, resulted in a still toxic material (55% ICG), whereas material treated in accordance with the invention (negative control) shows no cytotoxicity.

TABLE III

| Sample | Dose per 15 ml of Media | ICG % |
|---|---|---|
| Assay Control | 1.5 ml | 0 |
| Negative Control | 1.5 ml | −1 |
| Positive Control | 0.75 | 94 |
| Test Material | 1.5 | 55 |

Assay Control: Cell culture and medium without fluorocarbon.
Negative Control: Cell culture and medium with fluorocarbon purified in Example 1, Parts A and B.
Positive Control: Cell culture and medium with untreated sample of fluorocarbon.
Test Material: Cell culture and medium with fluorocarbon purified as in Examble 4.

EXAMPLE 5

The process of Example 1, Part A, is repeated in all essential respects except that the mixture of perfluorodimethyl adamantane and perfluoro-trimethylbicyclononane is refluxed for 15 minutes instead of 2 hours. The hydrogen level of the product is 8–10 ppm. This example shows that best results are obtained by extended refluxing, of the order of 1–2 hours or more, as in Part A of Example 1.

EXAMPLE 6

This example is another illustration of treatment of higher hydrogen content material.

(A) 100 units by weight of a perfluoro dimethyladamantane/perfluoro trimethylbicyclononane mixture, in a DMA:TMBCN weight ratio of approximately 2.6:1 and containing 401 ppm of hydrogen is treated with 50 units of 85% KOH (pellets) using two batches of 25 units each to keep the reaction from becoming thermally uncontrollable. The first 25 units of KOH is added to the fluorocarbon and the temperature of the mixture is gradually raised to 131° C. The second aliquot of 25 units of the 85% KOH is then added to the reaction mixture and the mixture is brought to reflux at 155° C. The intermediate product (I) of the reaction contains approximately 100 ppm hydrogen.

(B) 75 units of intermediate product (I) is treated with 37 units of 85% KOH (pellets) at reflux (174° C.) for two hours. The intermediate product (II) of the reaction contains 46 ppm hydrogen.

(C) 67 units of intermediate product (II) is treated with 33 units of 85% KOH (pellets) at reflux (174° C.) for two hours. The final product obtained is treated as in Part B of Example 1 and is found to contain less than 5 ppm hydrogen.

EXAMPLE 7

This example illustrates the effect of changing the KOH concentration. A mixture of perfluoro dimethyladamantane and perfluoro trimethylbicyclononane is distilled to obtain a heart cut mixture richer in perfluoro dimethyladamantane (3.5 to 1, perfluoro dimethyladamantane to perfluoro trimethylbicyclononane). The heart cut contains 52 ppm hydrogen. One aliquot (50 weight units) of this material is treated with 17.6 units of slightly pasty KOH (70% KOH, balance water) at between 196° C. and 204° C. for two hours in a pressurized reactor having a Teflon (trademark) liner. The product contains between 8 and 10 ppm hydrogen. A second aliquot (50 units) of the heart cut is treated with 25 units of syrupy KOH (50% KOH, balance water) at between 196° and 202° C. for two hours in the same lined pressurized reactor. The hydrogen level in the latter product actually increases, to approximately 76 ppm. This indicates that a KOH strength of at least about 70% is required for efficient hydrogen removal.

EXAMPLE 8

A crude mixture of perfluoro dimethyladamantane and perfluoro trimethylbicyclonane, similar to Example 1 and containing 64 ppm hydrogen is treated with NaOH (98.7 wt. %) pellets in three runs (50 wt. %, 25 wt.% and 12.5 wt. % of the pellets based on the crude fluorocarbon mixture) substantially as described in Part A of Example 1 except for a reflux temperature of about 165° C. After addition of water to the reaction mixture, the fluorocarbon phase is separated. The product of each run is found to contain less than 5 ppm hydrogen (limits of detection).

What is claimed is:

1. A method of purifying a mixture of perfluorocarbons containing 7 to 18 carbon atoms and other fluorocarbons containing hydrogen in the molecule, which comprises contacting said mixture with a base of a metal selected from alkali metals and alkaline earth metals and containing not more than about 30 wt. % water, at a temperature sufficient to react such other compounds with said base, thereby to convert such other fluorocarbons to reaction products, separating unreacted base, if present, and said reaction products from unreacted perfluorocarbons and subjecting the separated perfluorocarbons to a treatment with organic carbonyl compound consisting essentially of contacting said perfluorocarbons in liquid phase with an organic carbonyl compound in liquid phase to form a fluorocarbon phase and an organic carbonyl phase, and separating the phases to obtain a purified fluorocarbon phase.

2. The method of claim 1 wherein the base is an alkali metal hydroxide alkoxide or aryloxide.

3. The method of claim 1 wherein the base is potassium hydroxide.

4. The method of claim 3 wherein the potassium hydroxide is a pellet form and wherein the amount of said potassium hydroxide in pellet form is at least 15 wt. % based on the fluorocarbons.

5. The method of claim 4 wherein the fluorocarbons are in a liquid state.

6. The method of claim 5 wherein the first-mentioned contacting is effected at a temperature in the range from 165° C. to 250° C.

7. The method of claim 1 wherein the reaction products are separated by adding water to dissolve unreacted base and any metal fluoride formed, and the two phases which form are separated into a fluorocarbon phase and an aqueous phase.

8. The method of claim 7 wherein the fluorocarbon phase is further purified by washing with an organic solvent, the purified product is separated from the organic solvent mixture, and the product is washed with water to remove the solvent.

9. The method of claim 8 wherein the carbonyl compound is acetone and the organic solvent is a solution of acetic acid in methanol.

10. A method of purifying a fluorocarbon mixture comprising perfluorocarbons and other fluorocarbons which comprises contacting said mixture with a treating agent consisting essentially of a base of a metal selected from alkali metal and alkaline earth metal and containing not more than 30 wt.% water, at a temperature sufficient to react such other fluorocarbons with said base, thereby to convert such other fluorocarbons to reaction products, separating unreacted base, if present, and said reaction products from unreacted perfluorocarbons and subjecting the separated perfluorocarbons to a treatment with organic carbonyl compound consisting essentially of contacting said perfluorocarbons in liquid phase with an organic carbonyl compound in liquid phase to form a fluorocarbon phase and an organic carbonyl phase, and separating the phases to obtain a purified fluorocarbon phase.

11. Method according to claim 10 wherein said mixture is contacted with a treating agent consisting essentially of potassium hydroxide slurried in said mixture.

12. Method according to claim 1 wherein the first-mentioned contacting is effected at a temperature in the range from 165° C. to 250° C. for a period of 1 to 5 hours.

* * * * *